(12) United States Patent
Li

(10) Patent No.: US 7,774,141 B2
(45) Date of Patent: Aug. 10, 2010

(54) METHODS FOR THE IDENTIFICATION OF BUBBLE POINT PRESSURE

(75) Inventor: Baoyan Li, Spring, TX (US)

(73) Assignee: Baker Hughes Incorporated, Houston, TX (US)

( * ) Notice: Subject to any disclaimer, the term of this patent is extended or adjusted under 35 U.S.C. 154(b) by 325 days.

(21) Appl. No.: 12/016,052

(22) Filed: Jan. 17, 2008

(65) Prior Publication Data

US 2009/0187346 A1   Jul. 23, 2009

(51) Int. Cl.
*G01V 1/40*   (2006.01)
(52) U.S. Cl. ........................................... 702/11
(58) Field of Classification Search ............ 702/11, 702/12, 13, 100, 182–185
See application file for complete search history.

(56) References Cited

U.S. PATENT DOCUMENTS

| | | | |
|---|---|---|---|
| 5,635,631 A | 6/1997 | Yesudas et al. | |
| 6,758,090 B2 | 7/2004 | Bostrom et al. | |
| 6,941,804 B2 | 9/2005 | Hasem et al. | |
| 7,216,533 B2 | 5/2007 | McGregor et al. | |
| 2004/0260497 A1 | 12/2004 | DiFoggio et al. | |
| 2005/0268709 A1 | 12/2005 | McGregor et al. | |
| 2007/0119244 A1 | 5/2007 | Goodwin et al. | |
| 2007/0159625 A1 | 7/2007 | DiFoggio | |
| 2009/0165548 A1* | 7/2009 | Pop et al. ............... 73/152.51 |

* cited by examiner

*Primary Examiner*—Edward Raymond
(74) *Attorney, Agent, or Firm*—Cantor Colburn LLP

(57) ABSTRACT

A method includes acquiring formation fluid sample information including pressure, volume, and temperature. Monotonic formation fluid information is extracted from the formation fluid sample information and a pressure, volume, temperature information set is constructed. A curvature sequence is estimated using a first partial derivative and a second partial derivative of pressure with respect to volume. A first maxima is estimated from the curvature sequence, and the formation fluid property is estimated using the estimated first maxima. A method may include a volume acceleration sequence estimated using a first partial derivative and a second partial derivative of the volume with respect to pressure. A first maxima is estimated from the volume acceleration sequence, and the formation fluid property is estimated at least in part by using the estimated first maxima. A method may include establishing a first linear regression model and predicting a confidence interval.

20 Claims, 10 Drawing Sheets

```
ACQUIRE ORIGINAL FORMATION FLUID SAMPLING INFORMATION,
WHEREIN THE ORIGINAL FORMATION FLUID SAMPLING INFORMATION
INCLUDES PRESSURE, VOLUME, AND TEMPERATURE
                          ↓
EXTRACT MONOTONIC FORMATION FLUID INFORMATION FROM THE
ORIGINAL FORMATION FLUID SAMPLING INFORMATION
                          ↓
CONSTRUCT A PRESSURE, VOLUME, TEMPERATURE INFORMATION
SET FROM THE MONOTONIC FORMATION FLUID INFORMATION
                          ↓
ESTIMATE A CURVATURE SEQUENCE
                          ↓
ESTIMATE THE FIRST LOCAL MAXIMA OF THE CURVATURE SEQUENCE
                          ↓
ESTIMATE THE LOWER LIMIT OF THE BUBBLE POINT PRESSURE AT
THE FIRST LOCAL MAXIMA
```

METHODS FOR THE IDENTIFICATION OF BUBBLE POINT PRESSURE

BACKGROUND

1. Technical Field

The present disclosure generally relates to determination of a downhole formation fluid property and in particular to the determination of the bubble point pressure for a downhole formation fluid.

2. Background Information

Oil and gas wells have been drilled at depths ranging from a few thousand feet to as deep as five miles. Information about the subterranean formations traversed by the well borehole can be obtained by various techniques. Techniques used to obtain formation information include obtaining one or more core samples of the subterranean formations and obtaining fluid samples produced from the subterranean formations. Fluid samples are often retrieved from the borehole and tested in a rig-site or remote laboratory to determine properties of the fluid sample. Modern fluid sampling includes various downhole tests and sometimes fluid samples are retrieved for surface laboratory testing.

Properties of downhole formation fluids are of great importance to engineers. One important property in particular is the bubble point pressure of the downhole formation fluid. The bubble point pressure is the pressure at which gas evolves from the formation fluid, as the pressure of the formation fluid is decreased. The bubble point pressure is also a point to separate the status of the formation fluid into a saturated state and an undersaturated state. The formation fluid is at the saturated state where there is free gas in the formation fluid, otherwise the formation fluid is at the undersaturated state. To optimize the oil production, the pressure of a reservoir needs to be kept above the bubble point pressure. If the pressure drops below the bubble point during production, gas bubbles will form within the reservoir rock, which will decrease the relative permeability of the oil phase. Also, to precisely determine the bubble point pressure at the surface, the pressure of the formation fluid needs to be kept above the bubble point pressure, as it is transported to the surface.

Present methods used to determine the bubble point pressure of a formation fluid trap a volume of a formation fluid and gradually expand the volume and monitor how the pressure drops. Initially the pressure drops linearly with the expanding fluid volume. The estimated bubble point pressure is the pressure at which the pressure is no longer linearly related to the volume. In practice the current methods for estimating bubble point pressure are not as accurate and reliable as desired, because the formation fluid sampling test data can have uncontrollable noises and the formation sampling fluid may be contaminated. There is a need, therefore, for a method for more accurate estimation the bubble point pressure of a formation fluid.

SUMMARY

The following presents a general summary of several aspects of the disclosure in order to provide a basic understanding of at least some aspects of the disclosure. This summary is not an extensive overview of the disclosure. It is not intended to identify key or critical elements of the disclosure or to delineate the scope of the claims. The following summary merely presents some concepts of the disclosure in a general form as a prelude to the more detailed description that follows.

Disclosed is a method for estimating a formation fluid property. The method includes acquiring formation fluid sample information from a formation fluid sample, the formation fluid sample information including pressure, volume, and temperature of the formation fluid sample. Monotonic formation fluid information is extracted from the formation fluid sample information and a pressure, volume, temperature information set is constructed from the monotonic formation fluid sample information. A curvature sequence is estimated using a first partial derivative and a second partial derivative of the pressure with respect to the volume from the pressure, volume, temperature information set. A first maxima is estimated from the curvature sequence, and the formation fluid property is estimated at least in part by using the estimated first maxima.

In several aspects a method for estimating a formation fluid property includes acquiring formation fluid sample information from a formation fluid sample, the formation fluid sample information including pressure, volume, and temperature of the formation fluid sample. Monotonic formation fluid information is extracted from the formation fluid sample information and a pressure, volume, temperature information set is constructed from the monotonic formation fluid sample information. A volume acceleration sequence is estimated using a first partial derivative and a second partial derivative of the volume with respect to pressure from the pressure, volume, temperature information set. A first maxima is estimated from the volume acceleration sequence, and the formation fluid property is estimated at least in part by using the estimated first maxima.

In other aspects a method for estimating a formation fluid property includes acquiring formation fluid sample information from a formation fluid sample, the formation fluid sample information including pressure, volume, and temperature of the formation fluid sample. Monotonic formation fluid information is extracted from the formation fluid sample information and a pressure, volume, temperature information set is constructed from the monotonic formation fluid sample information. A first linear regression model is established with the pressure, volume, temperature information set. A confidence interval is estimated using the first linear regression model. A first pressure point, which is beyond the confidence interval, is determined. The fluid property is estimated at the last pressure point, which is within the confidence interval of the predicted linear regression model.

BRIEF DESCRIPTION OF THE DRAWINGS

For a detailed understanding of the present disclosure, reference should be made to the following detailed description of the several non-limiting embodiments, taken in conjunction with the accompanying drawings, in which like elements have been given like numerals and wherein.

DESCRIPTION OF EXEMPLARY EMBODIMENTS

Figure 1:
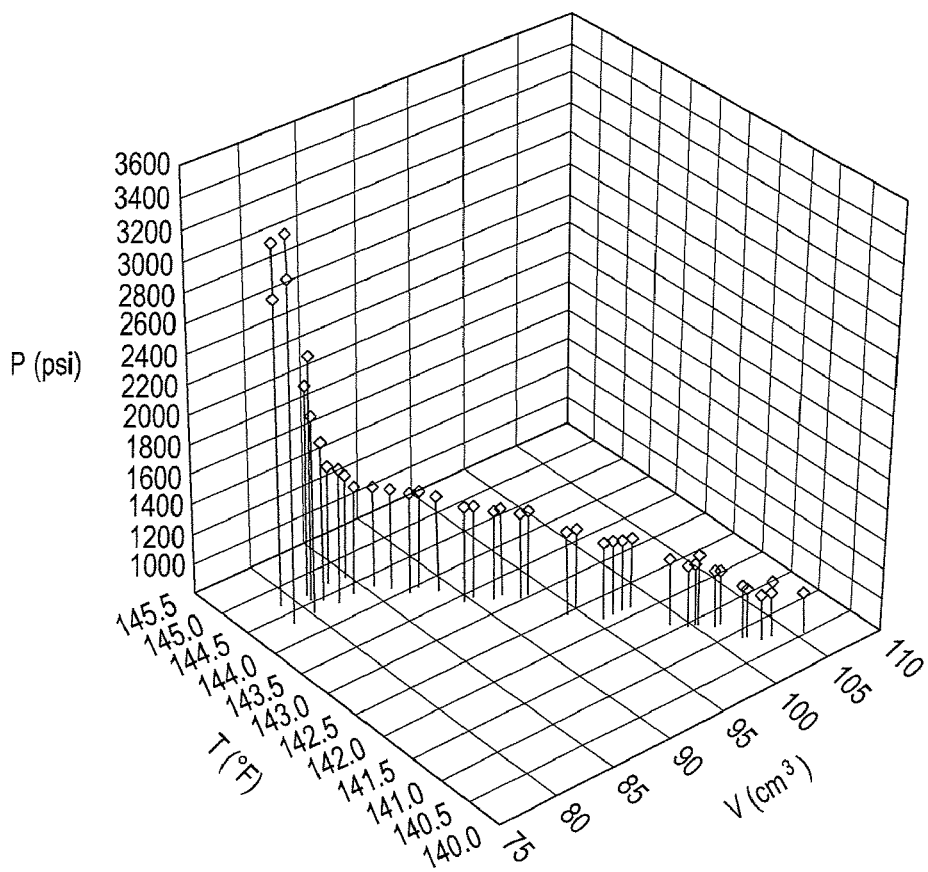
FIG. 1 is an illustrative spatial curve of P(V, T) for a formation fluid sampling test.

FIG. 1 shows an illustrative spatial curve of P(V, T) for a formation fluid sampling test. Properties of formation fluids can be determined either downhole or at the surface. The bubble point pressure of a formation fluid may be determined at the surface in a laboratory, for example. Determining properties downhole, rather than on the surface can provide benefits such as quality control and more accurate estimations of a formation fluid. Determining the bubble point pressure for a formation fluid can provide information as to the degree of contamination of the formation fluid, as well as provide a pressure above which the formation and the formation fluid as it is transported to the surface needs to be maintained. Determining the bubble point pressure of a formation fluid while the formation fluid is downhole can reduce the risk that gas may fall out of the formation fluid and consequently may provide a more accurate determination of the formation fluid's bubble point.

FIG. 1 shows the relationship between pressure (P), volume (V) and temperature (T) of a formation fluid sample. As shown in FIG. 1, it can be seen that the pressure depends on both the volume and temperature. As the volume increases the pressure decreases, where the volume is variable. As the pressure decreases the volume will increase, where the pressure is variable. The available data for the determination of the bubble point pressure at downhole conditions are the sampling sequences of time ($t_i$), pressure ($P_i$), volume ($V_i$), and temperature ($T_i$), where i=1, 2, . . . , $N_t$. $N_t$ is the total number of time sampling points. $P_i$, $V_i$, and $T_i$ are the measured pressure, volume, and temperature at time sampling point $t_i$, respectively.

Figure 2:
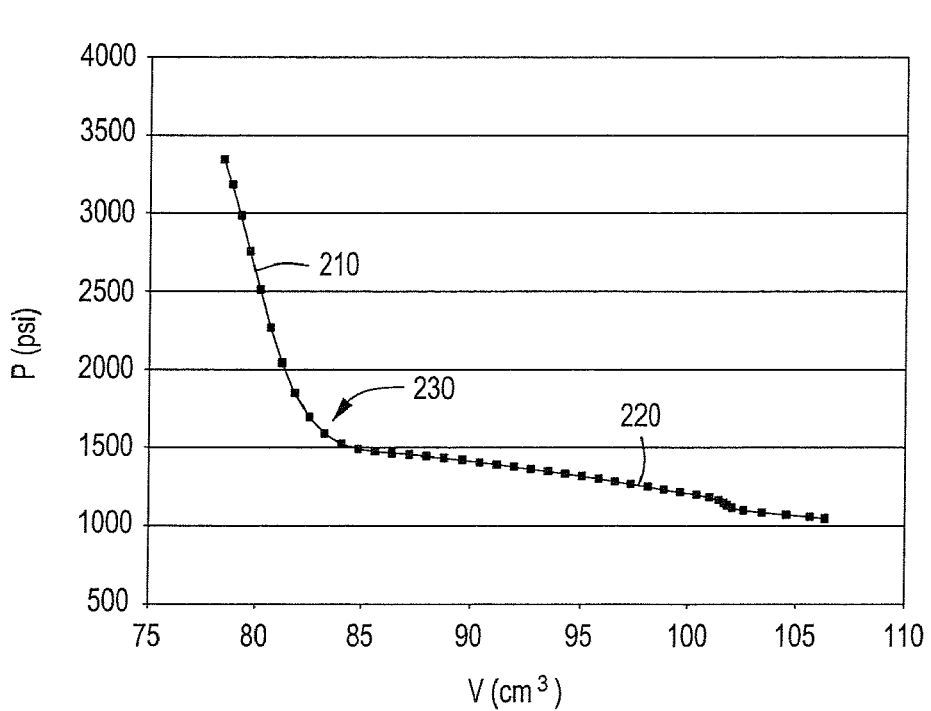
FIG. 2 is an illustrative plot of the spatial curve of FIG. 1 on the PV plane for the formation fluid sampling test.

FIG. 2 is an illustrative plot of the spatial curve of FIG. 1 on the PV plane for the formation fluid sampling test. As shown, from left to right, the PV plot 200 shows a smooth transition from a steeply-sloping line 210 to a gently-sloping line 220. The bubble point pressure is the pressure at which the steeply-sloping line 210 begins to transition to the gently-sloping line 220. The transition point between the steeply-sloping line and the gently-sloping line may be as generally indicated around arrow 230. This PV plot covers an interval of $N_t$ points as discussed above.

An accurate determination of bubble point pressure from formation sampling test data is a difficult and challenging problem. First, test data can have unpredictable measurement noises, as shown in FIG. 1 above. Second, the formation sampling fluid may be contaminated by the mud filtrate. Third, when the first gas bubble evolves from the formation fluid, the change in the volume of the downhole formation fluid sample is not significant, which makes an accurate calculation of the volume change difficult. Fourth, the linear part of the pressure spatial curve for the undersaturated state smoothly transitions to the nonlinear part for the saturated state, as seen in FIGS. 1 and 2. These issues can cause uncertainty and errors in determining the bubble point pressure for a formation fluid sample.

Rather than being constant, downhole temperatures may vary during the downhole formation fluid sampling test. Existing methods used to determine bubble point pressure assume that the temperature of the formation fluid sample is constant. If the temperature of the formation fluid sample is assumed as a constant, errors may be introduced to the estimated properties of the formation fluid sample. For example, the bubble point pressure, determined from a formation fluid sample downhole or at the surface by using such methods, may not be the bubble point pressure corresponding to the actual temperature.

In several embodiments the determination of the bubble point pressure may include identifying both a lower limit and an upper limit of the bubble point pressure. The lower and upper limits of the bubble point pressures may provide a range, within which the actual bubble point for the particular formation fluid sample will fall between. For example, a confidence of about 95% for the upper limit of the bubble point pressure may be estimated. In one embodiment two methods may be used to determine the lower limit of the bubble point pressure from formation fluid sampling test data. These two methods may include a curvature method and a volume acceleration method. In one embodiment a linear regression model may be used to determine the upper limit of the bubble point pressure from formation fluid sample information.

Depending on the state of the sampling fluid, which may be the undersaturated state or the saturated state, the measured pressure data can have different trends. For example, for the undersaturated state there is no free gas and the fluid volume increase rate may be relatively low, but for the saturated state the free gas can continuously evolve and the increase rate of the fluid volume may be relatively high.

The two different pressure trends join at a point where the pressure curve has the greatest bending degree. The bending degree of a curve can be indicated with the curvature. In one embodiment, the point where the two pressure trends join can be taken as the lower limit of the bubble point pressure. At this point on the pressure curve there is weak nonlinearity, which can indicate that the formation fluid sample has begun to enter the saturated state. The bubble point pressure of the formation fluid sample is higher than the lower limit bubble point pressure determined by this method. Therefore, this method provides an estimation as to the lower limit of the bubble point pressure for the formation sampling fluid.

Depending upon the quality of the formation fluid sampling data, for example, whether the data is smooth or noisy; one method over another, discussed and described below, may be preferable for estimating the lower limit of the bubble point pressure for a formation fluid sample. Various factors can influence the quality of the formation fluid sampling data, for example, the degree of contamination of the formation sampling fluid, mechanical tolerances of formation sampling tools, sensor drift, sampling resolution, and the like. Therefore, a particular set of formation fluid sampling data may be relatively smooth or noisy. The several non-limiting embodiments described herein allow for both smooth and noisy sampling data. For formation fluid sampling test data of different qualities, for example smooth versus noisy data, non-limiting embodiments may use different steps and/or additional steps. The different steps and or additional steps that may be used are described and discussed in detail below.

Figure 3:
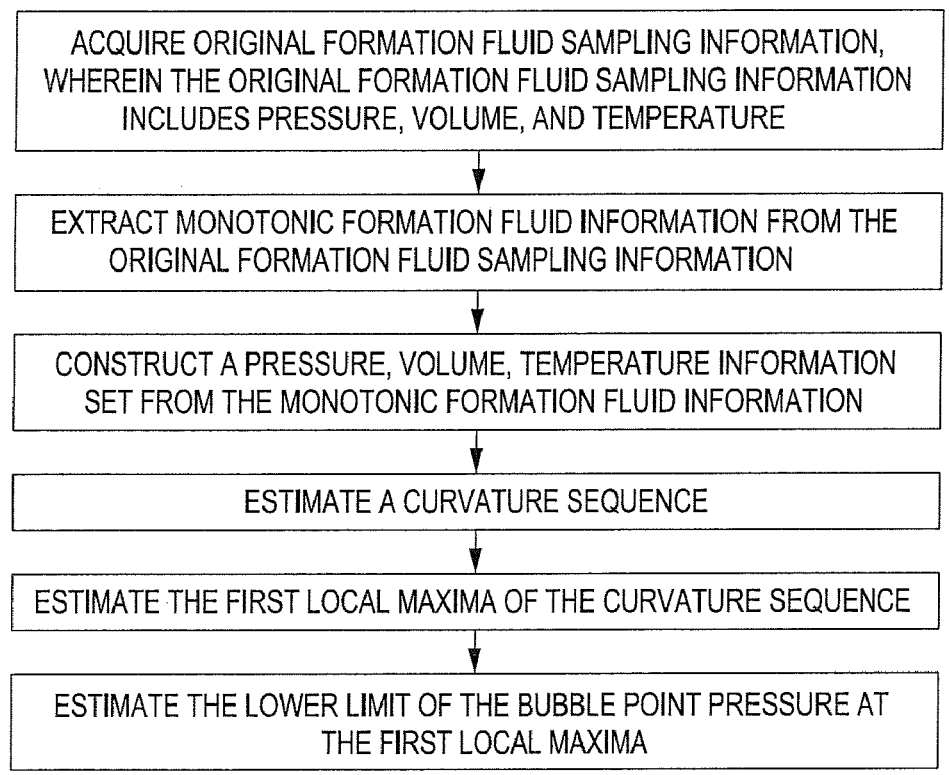
FIG. 3 illustrates an exemplary method for estimating the lower limit of the bubble point pressure using curvature for smooth formation fluid sampling data.

FIG. 3 illustrates an exemplary method for determining the lower limit of the bubble point pressure using curvature for smooth formation fluid sampling data. In several non-limiting embodiments, several steps may be carried out to estimate a lower limit of the bubble point pressure for a formation sampling fluid. In at least one embodiment, two or more steps may be combined into a single step.

In at least one non-limiting embodiment, the curvature may be computed based on estimations of the first partial derivative and the second partial derivative of the pressure with respect to formation fluid sample volume. The first partial derivative of pressure may be approximated by:

$$\left(\frac{\partial P}{\partial V}\right)_i \approx \frac{P_{i+1} - P_i}{V_{i+1} - V_i}, V_{i+1} > V_i, P_{i+1} < P_i,$$

where $P_i$ and $V_i$ are the pressure and the fluid volume at time $t_i$, respectively, and $(\partial P/\partial V)_i$ is the first partial derivative of pressure with respect to fluid volume at volume $V_i$. The second partial derivative of pressure may approximated by:

$$\left(\frac{\partial^2 P}{\partial V^2}\right)_i \approx \frac{\left(\frac{\partial P}{\partial V}\right)_{i+1} - \left(\frac{\partial P}{\partial V}\right)_i}{V_{i+1} - V_i}, V_{i+1} > V_i,$$

where $$\left(\frac{\partial^2 P}{\partial V^2}\right)_i$$

is the second partial derivative of pressure with respect to sample fluid volume at $V_i$. The curvature of the PV curve may be approximated by:

$$\kappa_i \approx \frac{\left(\frac{\partial^2 P}{\partial V^2}\right)_i}{1 + \left[\left(\frac{\partial P}{\partial V}\right)_i\right]^2},$$

where $\kappa_i$ is the curvature of the PV curve at fluid volume $V_i$.

In one non-limiting embodiment the first step to estimate the lower limit of the bubble point pressure may be to acquire original formation fluid sample information, which may include, but is not limited to, the sampling time, pressure, fluid volume, and temperature sub-sequences. The extracted sequences may be monotonic formation fluid information. For example, the monotonic formation fluid information may satisfy the condition $P_{i+1} < P_i$, i=1, 2, ..., M−1, where M is the length of a valid data sequence, which may be monotonic. By using monotonic formation fluid information bad data points are excluded from the original formation fluid information. The next step may include constructing a pressure, volume, temperature ("PVT") data set $\{P_i, V_i, T_i, i=1, 2, ..., M\}$ from valid test data set $\{t_i, P_i, V_i, T_i, i=1, 2, ..., M\}$. The curvature sequence $\{\kappa_i, i=1, 2, ..., M\}$, may be computed using the equation:

$$\kappa_i \approx \frac{\left(\frac{\partial^2 P}{\partial V^2}\right)_i}{1 + \left[\left(\frac{\partial P}{\partial V}\right)_i\right]^2},$$

with the pressure and volume data set $\{P_i, V_i, i=1, 2, ..., M\}$. The first local maxima at position $N_c$ of the curvature sequence may be found or estimated. The pressure $P_{Nc}$, volume $V_{Nc}$, and temperature $T_{Nc}$ of the first local maxima of the curvature sequence may be estimated. Finally, in at least one embodiment, the lower limit of the bubble point pressure may be estimated with $P_{Nc}$ and its corresponding volume $V_{Nc}$ and temperature.

Figure 4:
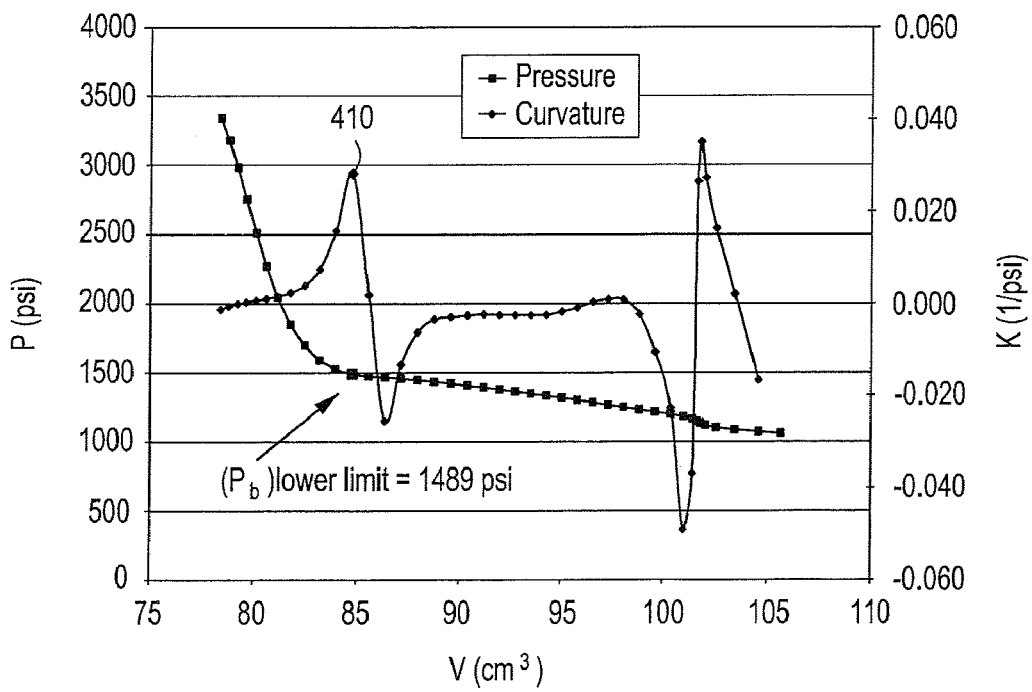
FIG. 4 is an illustrative pressure versus volume plot and the corresponding curvature plot for a formation fluid sampling test data set.

FIG. 4 is an illustrative pressure versus volume plot and the corresponding curvature plot for a smooth formation fluid sampling test data set. In several embodiments the lower limit of the bubble point pressure may be estimated by the curvature sequence $\kappa[P(V, T)]$ as discussed and described above. Here, local maxima are the points on the curvature plot at which the curvature sequence has maximum values in small intervals or regions. In the example in FIG. 4, the first local maxima 410 of the curvature curve is encountered as the volume increases and this first local maxima may be used to estimate the lower limit of the bubble point pressure. The local maxima 410 may be estimated and the corresponding pressure on the pressure versus volume plot may be used as the estimated lower limit of the bubble point pressure. The lower limit of the bubble point pressure for this particular formation fluid sample using the curvature method discussed above is 10,266 kPa (1489 psi). The lower limit of the bubble point pressure for the fluid sample may be representative of the lower limit of the bubble point pressure for the formation.

Figure 5:
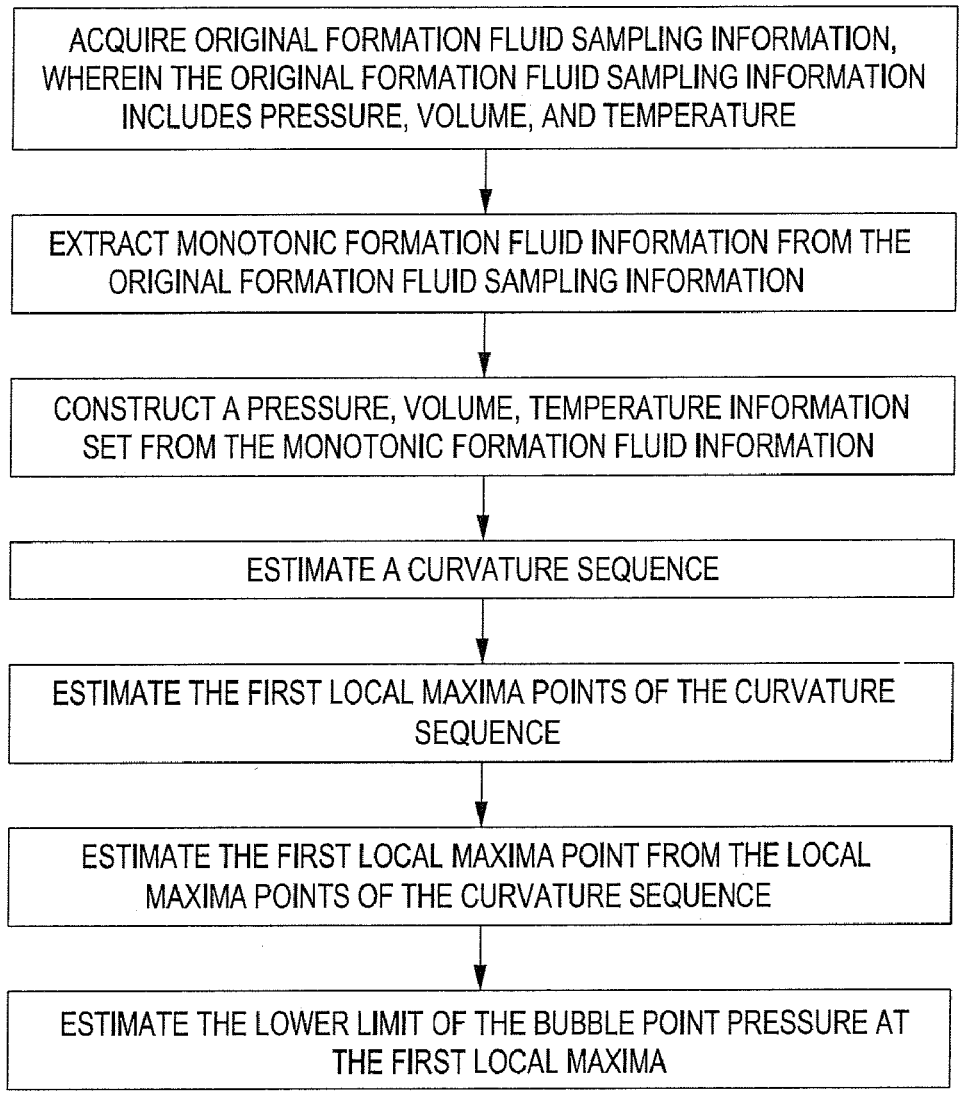
FIG. 5 illustrates an exemplary method for estimating the lower limit of the bubble point pressure using curvature for noisy formation fluid sample information.

FIG. 5 illustrates an exemplary method for determining the lower limit of the bubble point pressure using curvature for noisy formation fluid sample information. In several non-limiting embodiments, several steps may be carried out to estimate the lower limit of the bubble point pressure for a formation fluid sample. In at least one embodiment, two or more steps may be combined into a single step.

Figure 6:
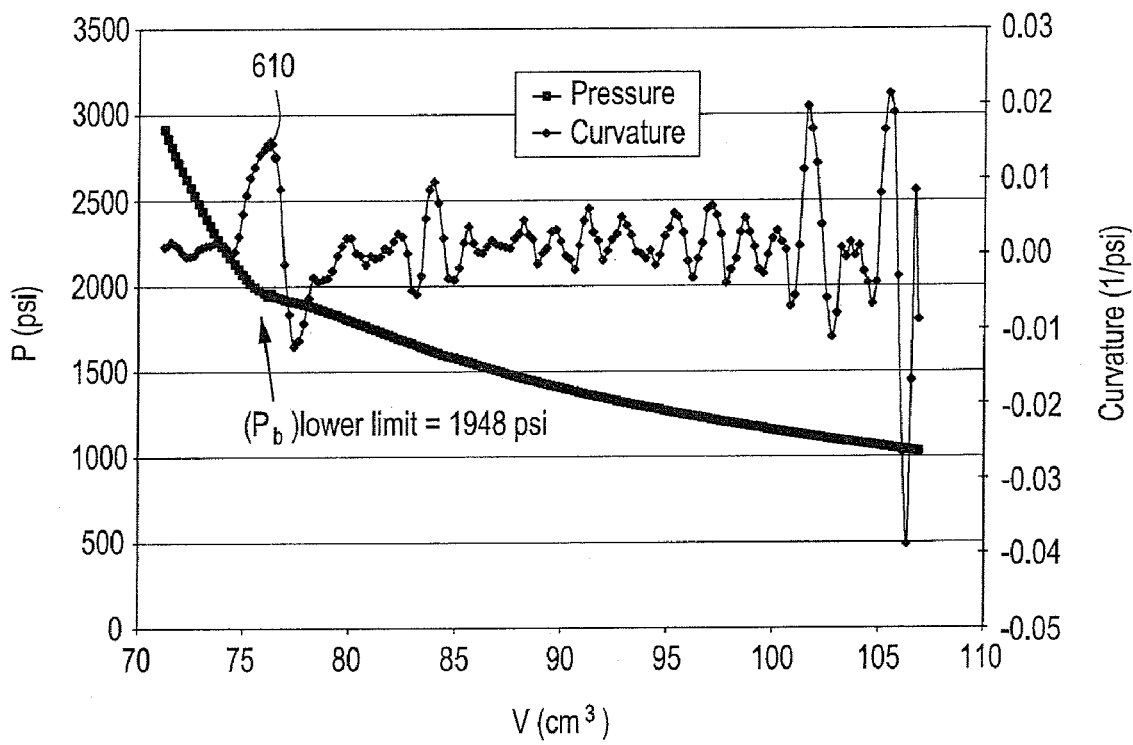
FIG. 6 is an illustrative pressure versus volume plot and the corresponding curvature plot for noisy formation fluid sample information.

In several situations the curvature sequence obtained from formation sampling test data may have noises, which may appear on a graph as shown in FIG. 6. In several non-limiting embodiment the first step to identify the lower limit of the bubble point pressure may be to acquire original formation fluid sample information, which may include, but is not limited to, the sampling time, pressure, fluid volume, and temperature sub-sequences. The extracted sequences may be monotonic formation fluid information. For example, the monotonic formation fluid information may satisfy the condition $P_{i+1} < P_i$, i=1, 2, ..., M−1, where M is the length of a valid data sequence, which is monotonic. By using monotonic formation fluid information bad data points are excluded from the original formation sampling fluid information. The PVT data set $\{P_i, V_i, T_i, i=1, 2, ..., M\}$ may be constructed from the valid test data set $\{t_i, P_i, V_i, T_i, i=1, 2, \ldots, M\}$. The curvature sequence $\{\kappa_i, i=1, 2, \ldots, M\}$, using:

$$\kappa_i \approx \frac{\left(\frac{\partial^2 P}{\partial V^2}\right)_i}{1+\left[\left(\frac{\partial P}{\partial V}\right)_i\right]^2},$$

may be computed, with the pressure and volume data set $\{P_i, V_i, i=1, 2, \ldots, M\}$. The local maxima sequence $\{\kappa_{max,l}, l=1, 2, \ldots, L_c\}$ of the curvature sequence $\{\kappa_i, i=1, 2, \ldots, M\}$ may be estimated. The first maxima point of the local maxima sequence of the curvature sequence may be found. The pressure $P_{lc}$, volume $V_{lc}$, and temperature $T_{lc}$ at position $l_c$ of the first local maxima of the local maxima sequence may be estimated. Finally the lower limit of the bubble point pressure may be estimated with $P_{lc}$ and its corresponding volume $V_{lc}$ and temperature $T_{lc}$. The first local maxima 610 of the local maxima sequence may be estimated and the corresponding pressure on the pressure versus volume plot may then be read and may be used as the lower limit of the bubble point pressure. FIG. 6 shows an illustrative pressure versus volume plot and the corresponding curvature plot for noisy formation fluid sample information. The first local maxima 610 can correspond to the pressure on the pressure versus volume plot of 10,266 kPa (1489 psi).

Figure 7:
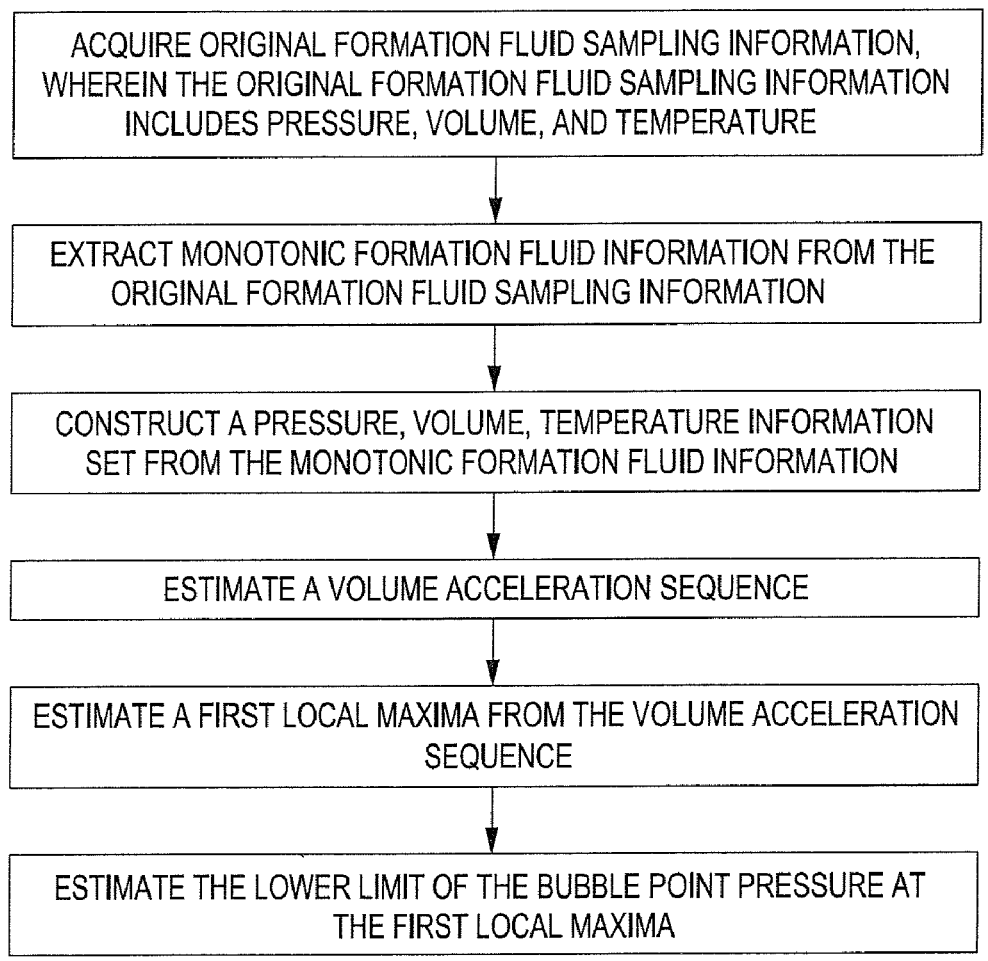
FIG. 7 illustrates an exemplary method for estimating the lower limit of the bubble pressure using volume acceleration for smooth formation fluid sample information.

FIG. 7 illustrates an exemplary method for determining the lower limit bubble pressure using a volume acceleration method for smooth formation fluid sample information. In several non-limiting embodiments, several steps may be carried out to estimate the lower limit of the bubble point pressure for a formation fluid sample. In at least one embodiment, two or more steps may be combined into a single step.

In several embodiments the lower limit of the bubble point pressure may be determined using a volume acceleration method. The volume acceleration of the formation fluid sample may be defined as the second partial derivative of the formation fluid volume with respect to pressure, seen as the equation:

$$a = \frac{\partial^2 V}{\partial P^2}.$$

The volume acceleration is a function of both the pressure and temperature. For an undersaturated formation fluid the volume acceleration should be zero because the undersaturated formation fluid has no free gas and the PVT relation is linear. However, free gas evolves from a saturated formation fluid and at this state the formation fluid has the nonlinear PVT relation and the nonlinear increase in volume. The nonlinear increase in volume implies that the volume acceleration rate is not zero, which can be seen in FIGS. 1, 2, 4, 6, and 8. In one embodiment, an ideal formation fluid sample would have a large increase in volume acceleration rate at the bubble point pressure. However, formation fluid samples may be contaminated, for example, with mud filtrate, and/or return fluid. Contamination of the formation fluid sample may cause the volume acceleration rate to gradually change from zero to non-zero rather than a sudden large increase in the volume acceleration rate.

In one non-limiting embodiment the volume acceleration may be estimated using the estimated first and second partial derivatives of the fluid volume with respect to pressure. The first partial derivative of fluid volume with respect to pressure may be estimated by the equation:

$$\left(\frac{\partial V}{\partial P}\right)_i \approx \frac{V_{i+1} - V_i}{P_{i+1} - P_i}, V_{i+1} > V_i, P_{i+1} < P_i,$$

where $P_i$ and $V_i$ are pressure and fluid volume at time $t_i$, respectively, and $$\left(\frac{\partial V}{\partial P}\right)_i$$

is the first partial derivative of the fluid volume with respect to pressure at pressure $P_i$. In at least one embodiment the volume acceleration may be approximated by:

$$\left(\frac{\partial^2 V}{\partial P^2}\right)_i \approx \frac{\left(\frac{\partial V}{\partial P}\right)_{i+1} - \left(\frac{\partial V}{\partial P}\right)_i}{P_{i+1} - P_i}, P_{i+1} < P_i,$$

where $$\left(\frac{\partial^2 V}{\partial P^2}\right)_i$$

is the volume acceleration at volume $V_i$.

In one non-limiting embodiment the first step to estimate the lower limit of the bubble point pressure may be to acquire original formation fluid sample information, which may include, but is not limited to, the sampling time, pressure, fluid volume, and temperature sequences. The extracted formation fluid sampling data sequences may be monotonic formation fluid information. For example, the monotonic formation fluid information may satisfy the condition $P_{i+1}<P_i$, $i=1, 2, \ldots, M-1$, where M is the length of a valid data sequence, which is monotonic. By using monotonic formation fluid information bad data points may be excluded from the original formation sampling fluid information. The next step may include constructing a PVT data set $\{P_i, V_i, T_i, i=1, 2, \ldots, M\}$ from the valid test data set $\{t_i, P_i, V_i, T_i, i=1, 2, \ldots, M\}$. The volume acceleration sequence $\{a_{v,i}, i=1, 2, \ldots, M\}$ may be computed using the pressure and volume data set $\{P_i, V_i, i=1, 2, \ldots, M\}$. The first local maxima for the volume acceleration sequence $\{a_{v,i}, i=1, 2, \ldots, M\}$ may be estimated or located. The pressure $P_{Na}$, volume $V_{Na}$, and temperature $T_{Na}$ at position $N_a$ of the first local maxima of the volume acceleration sequence may be estimated. The lower limit of the bubble point pressure may be estimated with $P_{Na}$ and its corresponding temperature $T_{Na}$.

Figure 8:
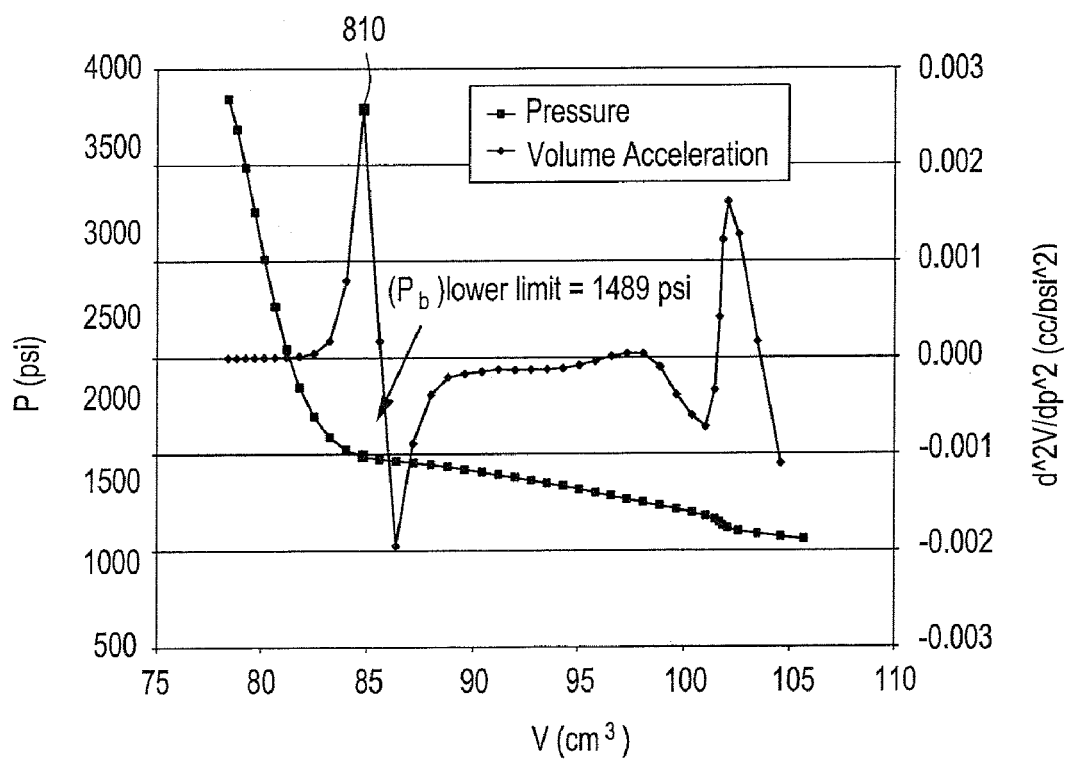
FIG. 8 is an illustrative pressure versus volume plot and the corresponding volume acceleration plot for formation fluid sample information.

FIG. 8 is an illustrative pressure versus volume plot and the corresponding volume acceleration plot for a formation fluid sampling test data set. The volume acceleration rate may have a local maxima 810 and the corresponding pressure on the pressure versus volume plot at the first local maxima 810 of the volume acceleration sequence may be taken as the lower limit of the bubble point pressure for the formation fluid sample evaluated. The bubble point pressure of the formation fluid sample will be larger than the lower limit of the bubble point pressure determined with this volume acceleration method. The lower limit of the bubble point pressure for this particular formation fluid sample, using the velocity acceleration method, is 10,266 kPa (1489 psi). The lower limit of the bubble point pressure for the fluid sample may be representative of the lower limit of the bubble point pressure for the formation. The estimated lower limit of the bubble point pressure corresponds to that determined with the curvature method.

Figure 9:
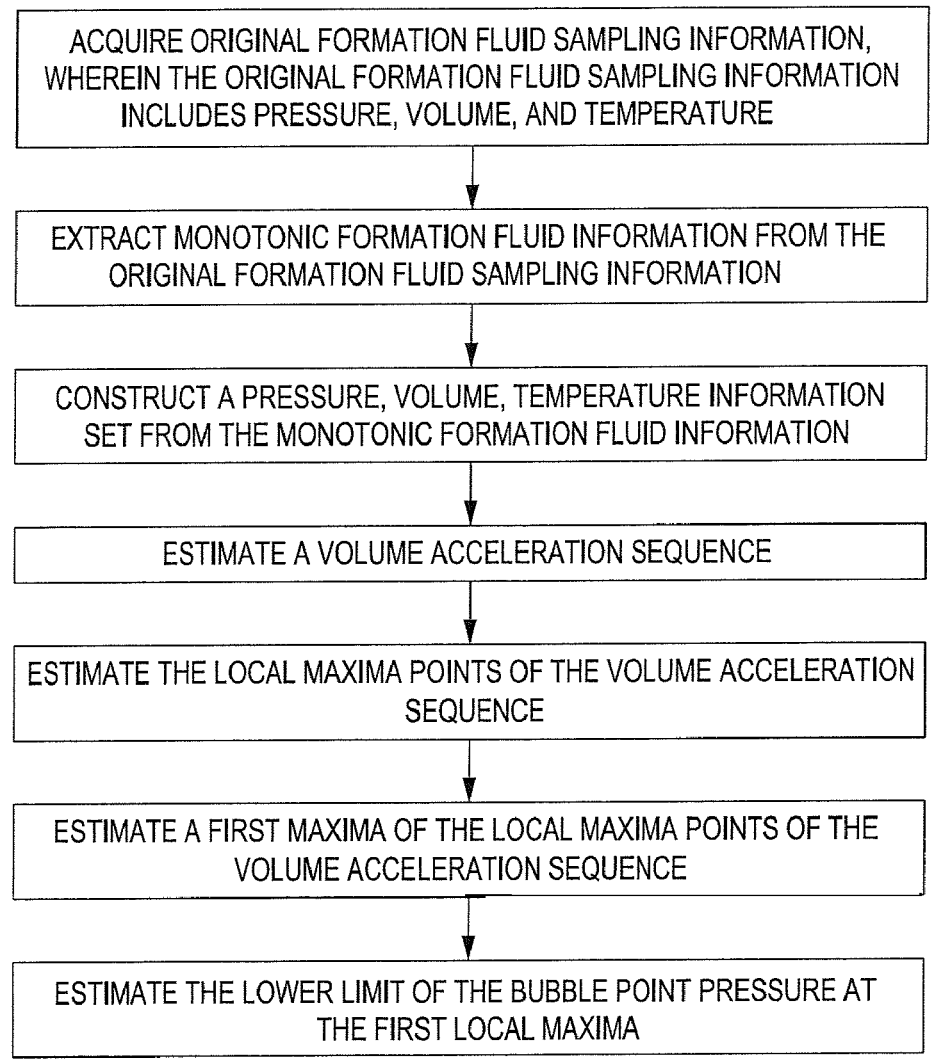
FIG. 9 illustrates an exemplary method for estimating the lower limit of the bubble point pressure using volume acceleration for noisy formation fluid sample information.

FIG. 9 illustrates an exemplary method for determining the lower limit of the bubble point pressure for a noisy formation fluid sampling test data using the volume acceleration method. In several non-limiting embodiments, several steps may be carried out to estimate a lower limit of the bubble point pressure for a sampling fluid. In at least one embodiment, two or more steps may be combined into a single step.

Figure 10:
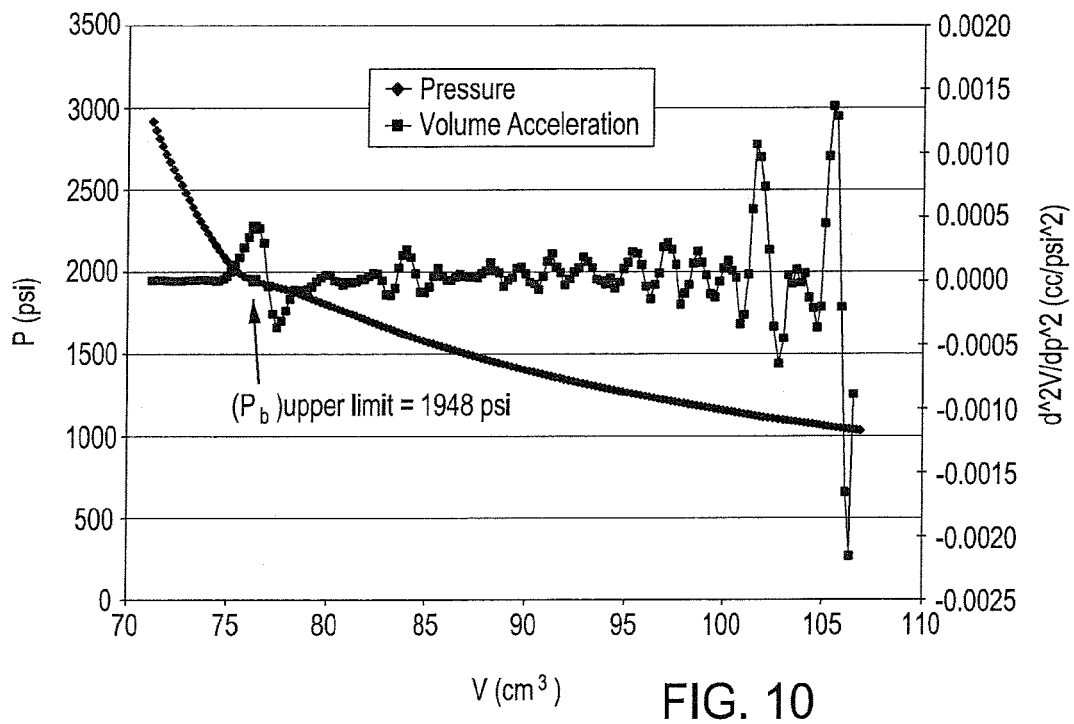
FIG. 10 is illustrative pressure and volume acceleration curves for noisy formation fluid sample information.

In one non-limiting embodiment the volume acceleration sequence obtained from formation fluid sampling test data may have noises, as shown in FIG. 10. In one non-limiting embodiment the first step to identify the lower limit of the bubble point pressure may be to acquire original formation fluid sample information, which may include, but is not limited to, the sampling time, pressure, fluid volume, and temperature sub-sequences. The extracted sequences may be monotonic formation fluid information. For example, the monotonic formation fluid information may satisfy the condition $P_{i+1} < P_i$, i=1, 2, ..., M−1, where M is the length of a valid data sequence, which is monotonic. By using the monotonic formation fluid information, bad data points may be excluded from the original formation sampling fluid information. The next step may include constructing a PVT data set $\{P_i, V_i, T_i, i=1, 2, \ldots, M\}$ from valid test data set $\{t_i, P_i, V_i, T_i, i=1, 2, \ldots, M\}$. The volume acceleration sequence $\{a_{v,i}, i=1, 2, \ldots, M\}$, may be computed using:

$$\left(\frac{\partial^2 V}{\partial P^2}\right)_i \approx \frac{\left(\frac{\partial V}{\partial P}\right)_{i+1} - \left(\frac{\partial V}{\partial P}\right)_i}{P_{i+1} - P_i}, \quad P_{i+1} < P_i,$$

with the constructed PVT data set $\{P_i, V_i, i=1, 2, \ldots, M\}$. The local maxima points of the volume acceleration sequence $\{a_{v,i}, i=1, 2, \ldots, M\}$ may be estimated. The first maxima point of the local maxima sequence $\{a_{v,max,l}, l=1, 2, \ldots, L_a\}$ of the volume acceleration may be estimated. The pressure $P_{la}$, volume $V_{la}$, and temperature $T_{la}$ at position $l_a$ of the first local maxima of the local maxima sequence may be estimated. The lower limit of the bubble point pressure may be estimated using $P_{la}$ and the corresponding temperature with $T_{la}$. Illustrative pressure and volume acceleration curves for a noisy formation fluid sampling test data set may be as shown in FIG. 10.

In at least one embodiment the lower limit of the bubble point for a formation fluid sample estimated for smooth and/or noisy sample information using the curvature method, volume acceleration method, or both may be used as a reference pressure for maintaining either a formation pressure or a formation fluid sample pressure above the bubble point. For example, a formation fluid as it is being transported to the surface can be monitored. A reservoir engineer can increase the pressure of either the formation or the formation fluid sample when the pressure begins to decrease. The pressure of a formation may be adjusted by pumping or injecting the fluid of high pressure to the formation. Enough fluid may be intjected to increase and/or maintain the pressure of the formation above the bubble point pressure of the formation.

Figure 11:
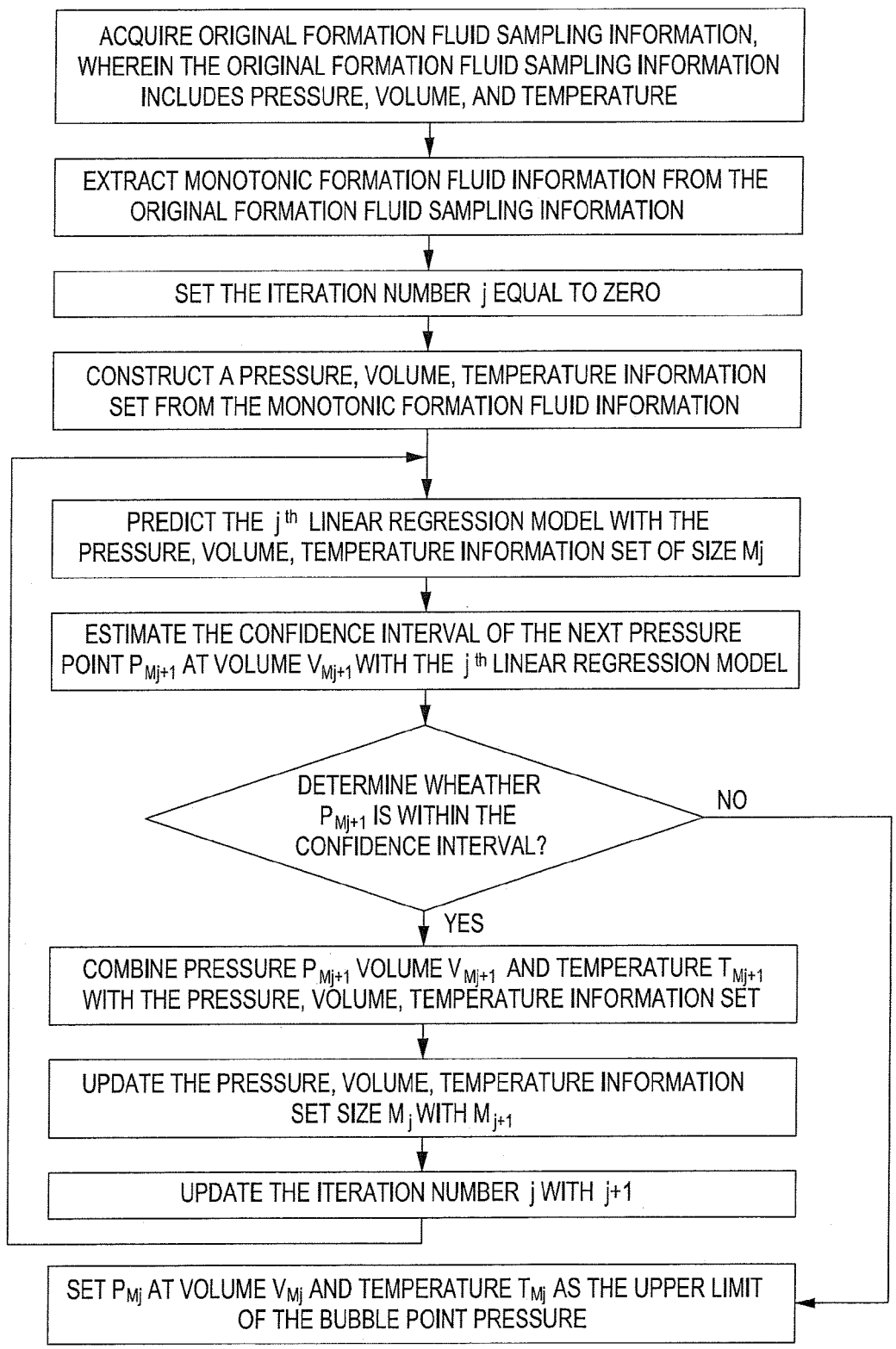
FIG. 11 illustrates an exemplary method for estimating the upper limit of the bubble point pressure using a linear regression model.

FIG. 11 illustrates an exemplary method for determining the upper limit of the bubble point pressure using a linear regression model. In several non-limiting embodiments, several steps may be carried out to estimate the upper limit of the bubble point pressure for a formation fluid sample. In at least one embodiment, two or more steps may be combined into a single step.

In several embodiments a statistical method may be used to objectively identify the upper limit of the bubble point pressure for a formation fluid sample. The upper limit of the bubble point pressure for the fluid sample may be representative of the upper limit of the bubble point pressure for the formation. The statistical method may be used to build up the linear regression model with the test data of a formation fluid at the undersaturated state. The confidence interval may be predicted with the linear regression model to identify the pressure point where the formation enters the saturated state. In one embodiment the measured pressure and volume data set $\{P_{ti}, V_{ti}, i=1, 2, \ldots, M_j\}$ may be used to construct the linear regression model, which may be represented by the equation:

$$P = \beta_0 + \beta_1 V + \epsilon, \quad \epsilon \sim N(0, \sigma^2),$$

where $\beta_0$ is a constant, $\beta_1$ is the constant coefficient of fluid volume V, $\epsilon$ is the Gaussian white observation noise with zero mean, and $\sigma^2$ is the variance of noise $\epsilon$. The vector format of the linear regression model established from the measured pressure and volume data set $\{P_{ti}, V_{ti}, i=1, 2, \ldots, M_j\}$ may be represented by the equation:

$$p = V\beta + \epsilon,$$

where $$p = \begin{bmatrix} P_{t_1} \\ P_{t_2} \\ \vdots \\ P_{t_{M_j}} \end{bmatrix}$$

is the pressure observation vector, $$V = \begin{bmatrix} 1 & V_{t_1} \\ 1 & V_{t_2} \\ \vdots & \vdots \\ 1 & V_{t_{M_j}} \end{bmatrix}$$

is the experimental matrix, $$\beta = \begin{bmatrix} \beta_0 \\ \beta_1 \end{bmatrix}$$

is the coefficient vector, $$\varepsilon = \begin{bmatrix} \varepsilon_1 \\ \varepsilon_2 \\ \vdots \\ \varepsilon_{M_j} \end{bmatrix}$$

is the observation error vector. The least square estimator of coefficient vector $\beta$ is:

$$\hat{\beta} = (V'V)^{-1}V'p$$

where (') denotes the transport operation of a matrix. The unbiased estimator of variance $\sigma^2$ may be given by $$\hat{\sigma}^2 = \frac{SS_e}{M_j - 1},$$

where $SS_e$ is the residual sum of squares, which may be calculated by $$SS_e = e'e = (p-\hat{p})'(p-\hat{p}) = p'p - \hat{\beta}V'p,$$

where $\hat{p}$ is the predicted pressure vector and $\hat{p} = V'\hat{\beta}$.

For a future volume observation point $V_0$, the mean pressure response may be predicted by:

$$\hat{p}(V_0) = v_0'\hat{\beta},$$

where $$v_0 = \begin{bmatrix} 1 \\ V_0 \end{bmatrix}.$$

The $100(1-\alpha)\%$ percent confident interval of the mean pressure response at this future volume observation point $V_0$ may be predicted by:

$$\hat{p}(V_0) - t_{\alpha/2, n-1}\sqrt{\hat{\sigma}^2[v_0'(V'V)^{-1}v_0]} \leq$$
$$\mu_{p|V_0} \leq \hat{p}(V_0) + t_{\alpha/2, n-1}\sqrt{\hat{\sigma}^2[v_0'(V'V)^{-1}v_0]},$$

where $t_{\alpha/2, n-1}$ is the random variable value, with t distribution value of $\alpha/2$ and freedom degree of n−1.

This statistical method used to estimate the upper limit of the bubble point pressure can be an iterative method. The linear regression model may be established from the first valid $M_j$ time sampling point of the valid test data. The confidence interval for the $(M_j+1)^{th}$ pressure sampling point may be predicted with the established linear regression model. If the measured pressure at the $(M_j+1)^{th}$ volume point is beyond the predicted confidence interval for this sampling point, the pressure at the $M_j^{th}$ volume point may be considered as the upper limit of the bubble point pressure and the iteration process may be stopped. If the measured pressure at the $(M_j+1)^{th}$ volume point is within the predicted confidence interval, sampling point information $P_{t_{Mj+1i}}, V_{t_{Mj+1i}}, T_{t_{Mj+1i}}$ may be combined with $\{P_{t_i}, V_{t_i}, T_{t_i}, i=1, 2, \ldots, M_j\}$ and $M_j$ may be updated with $M_j+1$ and then continue with the next iteration.

In one non-limiting embodiment the first step may be to acquire the original formation fluid sample information, which may include, but is not limited to, the sampling time, pressure, fluid volume, and temperature sub-sequences. The extracted sequences may be monotonic formation fluid information. For example, the monotonic formation fluid information may satisfy the condition $P_{i+1} < P_i, i=1, 2, \ldots, M-1$, where M is the length of a valid data sequence, which may be monotonic. By using the monotonic formation fluid information bad data points, non-monotonic for example, may be excluded from the original formation fluid information. The iteration number j may be set to zero (0). The next step may include constructing a PVT data set $\{P_i, V_i, T_i, i=1, 2, \ldots, M\}$ from valid test data set $\{t_i, P_i, V_i, T_i, i=1, 2, \ldots, M\}$. The $j^{th}$ linear regression model may be established with pressure and volume data set $\{p_i, V_i, i=1, 2, \ldots, M_j\}$ using $\hat{\beta} = (V'V)^{-1}V'p$. The confidence interval of the next pressure point $P_{Mj+1}$ at volume $V_{Mj+1}$ may be predicted with the $j^{th}$ linear regression model using:

$$\hat{p}(V_0) - t_{\alpha/2, n-1}\sqrt{\hat{\sigma}^2[v_0'(V'V)^{-1}v_0]} \leq$$
$$\mu_{p|V_0} \leq \hat{p}(V_0) + t_{\alpha/2, n-1}\sqrt{\hat{\sigma}^2[v_0'(V'V)^{-1}v_0]}.$$

In at least one embodiment it may be determined whether the $P_{Mj+1}$ is within its predicted confidence interval. If $P_{Mj+1}$ is beyond its predicted confidence interval then $P_{Mj}$ at temperature $T_{Mj}$ may be set as the upper limit of the bubble point pressure and the iterative process may be stopped. In at least one embodiment, if the $P_{Mj+1}$ is within its predicted confidence interval then the pressure $P_{Mj+1}$, volume $V_{Mj+1}$, and temperature $T_{Mj+1}$ may be combined with the PVT data set $\{P_i, V_i, T_i, i=1, 2, \ldots, M_j\}$. The size $M_j$ of the PVT data set may be updated with $M_j+1$. The iteration number j may be updated with j+1. In at least one embodiment the $j^{th}$ linear regression model may be established with the pressure and volume data set $\{P_i, V_i, i=1, 2, \ldots, M_j\}$, using $\hat{\beta} = (V'V)^{-1}V'p$. The iterative process of estimating $P_{Mj+1}$ may be continued until $P_{Mj+1}$ is beyond the predicted confidence interval.

Figure 12:
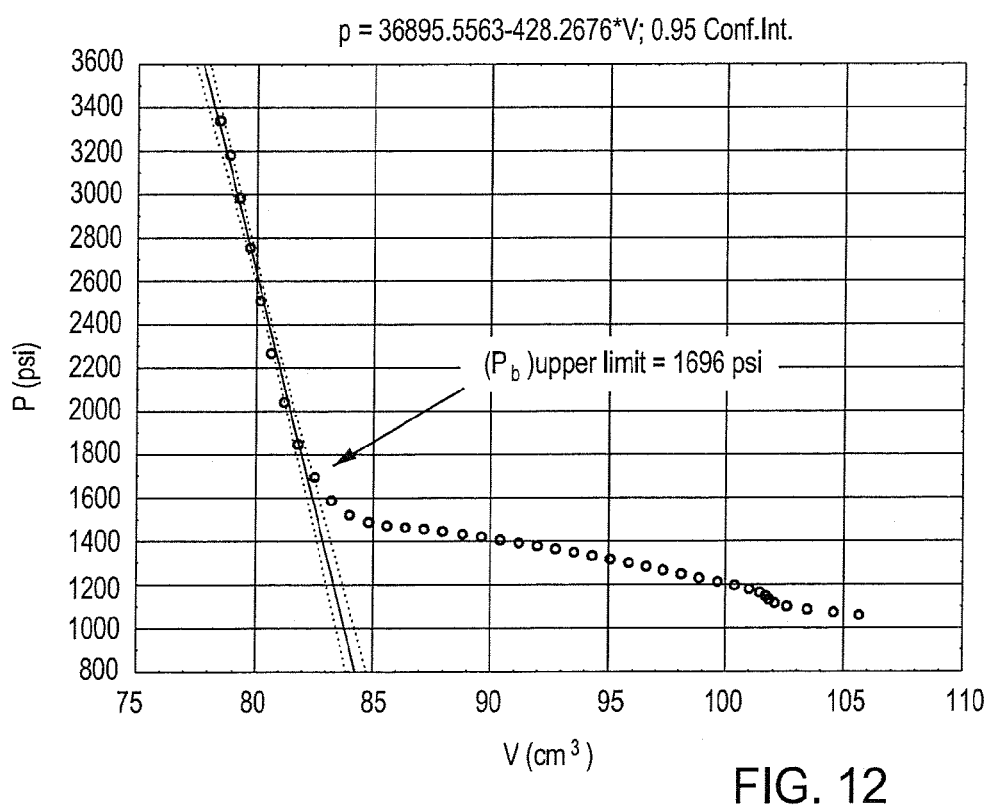
FIG. 12 is an illustrative plot of a linear regression model and its 95% confidence interval for formation fluid sample information.

FIG. 12 is an illustrative plot of the linear regression model and a 95% confidence level for a formation fluid sampling test data sub-set. FIG. 12 shows the upper limit of the bubble point pressure for a formation fluid sample using this statistical method is 11,694 kPa (1696 psi). The difference between the lower limit and the upper limit of the bubble point pressure is 11,691 kPa−10,266 kPa=1,425 kPa (207 psi). The bubble point pressure for the particular formation to be evaluated will be between the lower and upper limits.

Figure 13:
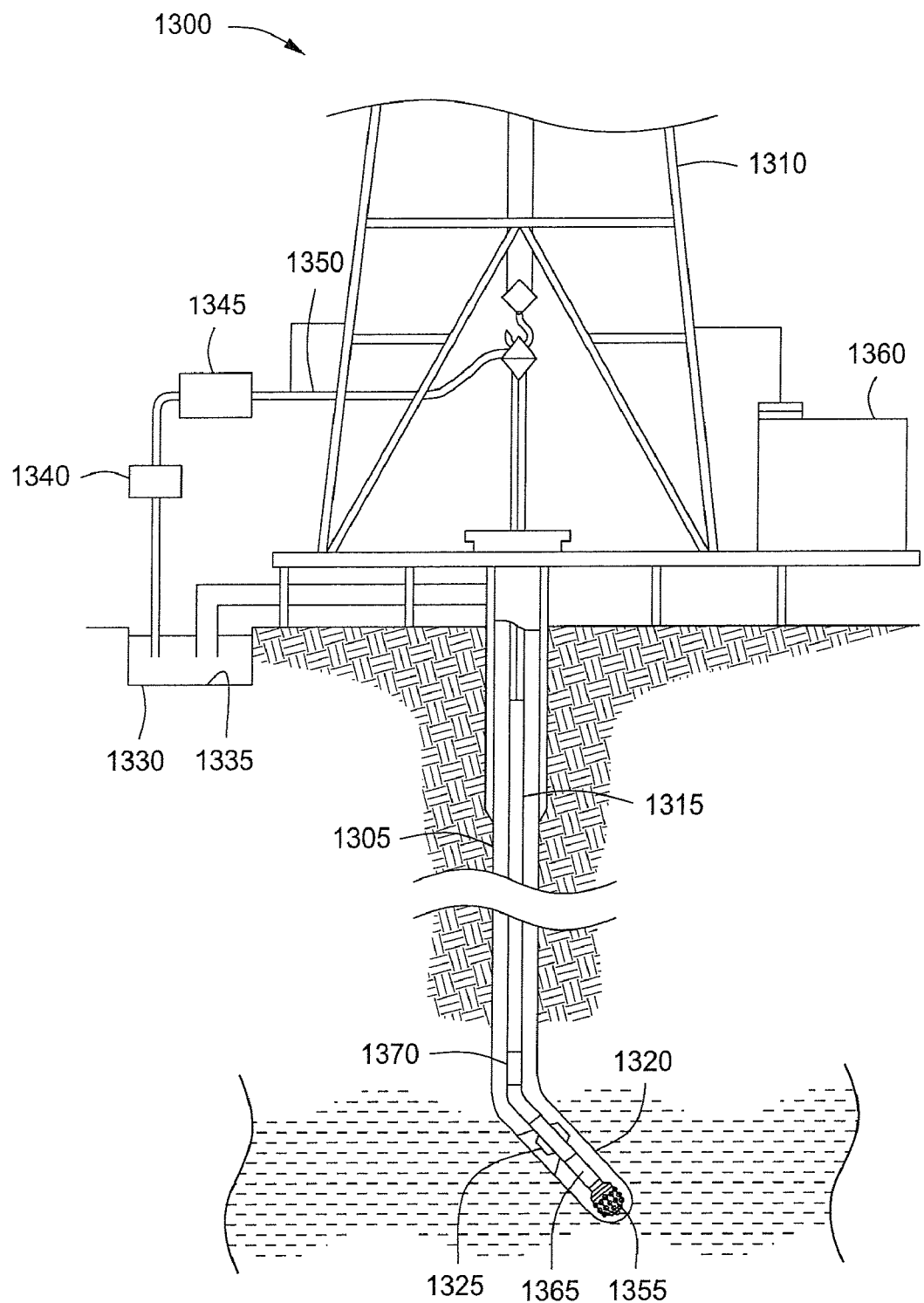
FIG. 13 is an elevation view of a simultaneous drilling and logging system 800 that may incorporate non-limiting embodiments of the disclosure.

FIG. 13 is an elevation view of a simultaneous drilling and logging system 1300 that may incorporate non-limiting embodiments of the disclosure. A well borehole 1305 is drilled into the earth under control of surface equipment including a drilling rig 1310. In accordance with a conventional arrangement, drilling rig 1310 includes a drill string 1315. The drill string 1315 may be a coiled tube, jointed pipes or wired pipes as understood by those skilled in the art. In one example, a bottom hole assembly ("BHA") 1320 may include a tool 1325 according to the disclosure. In other non-limiting embodiments a wireline may be used to carry the tool 1325 downhole. A suitable wireline tool for use with the present invention may be as disclosed in U.S. Pat. No. 5,635,631 which is hereby incorporated by reference in its entirety.

While-drilling tools will typically include a drilling fluid 1330 circulated from a mud pit 1335 through a mud pump 1340, past a desurger 1345, through a mud supply line 1350. The drilling fluid 1330 flows down through a longitudinal central bore in the drill string, and through jets (not shown) in the lower face of a drill bit 1355. Return fluid containing drilling mud, cuttings and formation fluid flows back up through the annular space between the outer surface of the drill string and the inner surface of the borehole to be circulated to the surface where it is returned to the mud pit.

The system 1300 in FIG. 13 may use any conventional telemetry methods and devices for communication between the surface and downhole components. In the embodiment shown mud pulse telemetry techniques are used to communicate data from downhole to the surface during drilling operations. In another embodiment, electrical signals via a wire or optical signals via a fiber optic cable may be used to transmit data from the one or more tools 1325 to the surface. An information processor 1360 may be used for processing commands and other information used in the drilling operations or for carrying out the several method embodiments described herein.

If applicable, the drill string 1315 can have a downhole drill motor 1365 for rotating the drill bit 1355. In several embodiments, the while-drilling tool 1325 may incorporate any known PVT sampling tool for measuring one or more properties of a formation fluid. In one non-limiting embodiment, the tool 1325 may include any of the configurations as described below and shown in FIG. 14.

A telemetry system 1370 may be located in a suitable location on the drill string 1315 such as above the tool 1325. The telemetry system 1370 may be used to receive commands from, and send data to, the surface via the mud pulse telemetry described above or by other communication techniques known in the art. For example, acoustic pipe telemetry and/or wired pipe telemetry may be used.

The surface information processor 1360 may include a processor, a computer-readable media such as a memory for storing data, a data recorder, and other peripherals. The surface controller 1360 may also respond to user commands entered through a suitable device, such as a keyboard. In one non-limiting embodiment, the BHA 1320 contains various sensors and logging-while-drilling (LWD) devices incorporating aspects of the disclosure to provide information about the formation, downhole drilling parameters and the mud motor.

Figure 14:
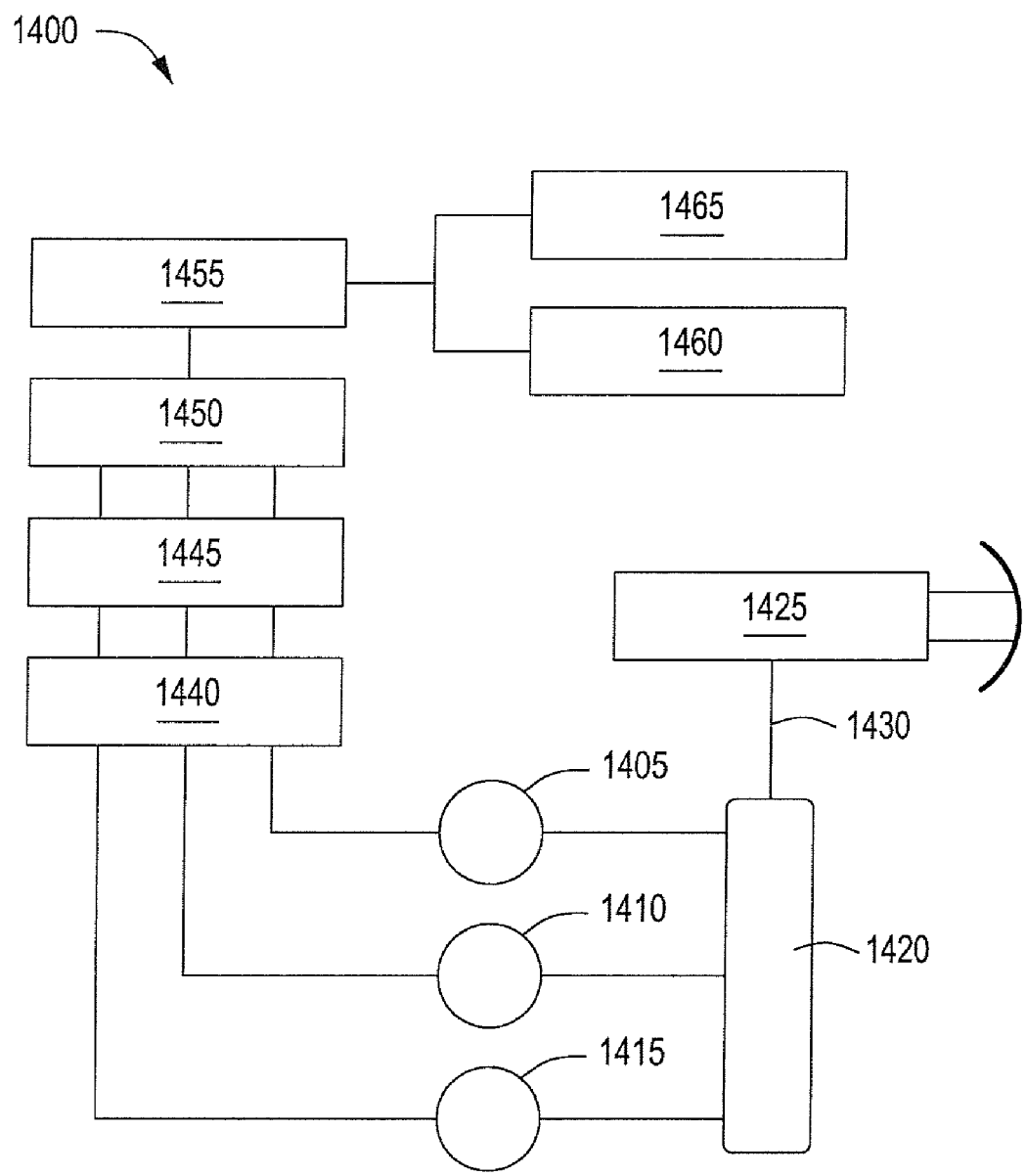
FIG. 14 is a schematic illustration of a measurement and control circuit that may be used according to the present disclosure.

FIG. 14 is a schematic illustration of a measurement and control circuit 1400 that may be used according to the present disclosure. The measurement and control circuit includes one or more pressure sensors 1405, volume sensors 1410, and temperature sensors 1415 to measure parameters such as the pressure, volume, and/or temperature for a formation fluid sample which may be introduced to a fluid sample chamber 1420. In one embodiment a formation fluid sample may be introduced to the fluid sample chamber 1420 via an extendable probe 1425. The extendable probe may extend from the tool into the borehole where it can collect a formation fluid sample, which can then be introduced via line 1430 into the fluid sample chamber 1420. In at least one embodiment original formation fluid sample information may be acquired via the sensors 1405, 1410, and/or 1415, which may include, but is not limited to, pressure, volume, and temperature information. In one non-limiting embodiment the formation fluid sample may be introduced to the fluid sample chamber 1420. The fluid sample chamber may have a piston or other device which can be moved inward or outward thereby changing the volume of the fluid sample chamber 1420. The volume of the fluid sample chamber 1420 at a give time can be recorded along with the pressure and temperature. The volume of the fluid sample chamber 1420 may be increased at a variable or constant rate with pressure readings taken at predetermined volumes as the volume is increased. In one embodiment, the original formation fluid sample information for a formation fluid sample may be acquired while downhole. In another embodiment, the fluid sample may be first brought to the surface where the original formation fluid sample information may then be acquired.

In one non-limiting embodiment, the sensors 1405, 1410, 1415 may be coupled to transmit sensor output signals to respective signal conditioning circuits 1440 for filtering the signals as needed. The signal conditioning circuits may be coupled to transmit conditioned signals to an analog-to-digital converter (ADC) circuit 1445 where any of the sensors does not provide a digital output signal. ADC circuit 1445 output signals may be fed into a multiplexer circuit 1450 or into a multi-channel input of an information processor 1455. The information processor 1455 may then feed processed signals to a memory 1460 and/or to a transceiver circuit 1465. The information processor 1455 may be located on the tool 1325, drill string 1315, or may be a surface information processor such as the information processor 1360 described above and shown in FIG. 13. When using a downhole information processor, commands may be received via the transceiver circuit 1465. Downhole command and control of the tool 1325 and of the extendable probe 1425 may be accomplished using programmed instructions stored in the memory 1460 or other computer-readable media that are then accessed by the processor 1455 and used to conduct the several methods and downhole operations disclosed herein. The information obtained from the sensors may be processed down-hole using the processor 1455 with the processed information being stored downhole in the memory 1460 for later retrieval. In other embodiments, the processed information may be transmitted to the surface in real time in whole or in part using the transceiver 1465.

In one non-limiting embodiment the data or information collected by the sensors 1405, 1410, and/or 1415 may be stored in any suitable medium. In one example, the medium includes a computer-readable storage medium. In at least one embodiment, the time that each information reading is acquired by the one or more sensors may be recorded and stored along with the information. The recording of the time each particular set of information is recorded may be used in estimating one or more formation fluid properties, for example the lower limit and upper limit bubble point pressures as discussed and described above. Estimating one or more fluid properties using the information may be done using any suitable information processing device, for example by a computer. In at least one embodiment, the one or more estimated fluid properties may be displayed in any suitable medium, for example on a computer screen or printed on a suitable printing medium such as paper.

The present disclosure is to be taken as illustrative rather than as limiting the scope or nature of the claims below. Numerous modifications and variations will become apparent to those skilled in the art after studying the disclosure, including use of equivalent functional and/or structural substitutes for elements described herein, use of equivalent functional couplings for couplings described herein, and/or use of equivalent functional actions for actions described herein. Such insubstantial variations are to be considered within the scope of the claims below.

What is claimed is:

1. A method for estimating a formation fluid property comprising:

acquiring formation fluid information, the formation fluid information including pressure and volume;

extracting monotonic formation fluid information from the formation fluid information;

constructing an information set from the monotonic formation fluid information;

estimating a first partial derivative and a second partial derivative of the pressure with respect to the volume from the information set;

estimating a first maxima from a curvature sequence; and estimating the formation fluid property at least in part by using the estimated first maxima.

2. A method according to claim 1 further comprising searching a set of local maxima points from the curvature sequence before estimating the first maxima.

3. A method according to claim 1 further comprising storing a value of the estimated formation fluid property in a computer-readable storage medium.

4. A method according to claim 1, wherein the formation fluid property comprises a lower limit of the bubble point pressure.

5. A method according to claim 1, wherein the formation fluid information is acquired from formation fluid while downhole or at the surface.

6. A method according to claim 1, wherein the formation fluid property is a pressure, wherein the pressure is estimated using the information set at the pressure corresponding to the first maxima of the curvature sequence.

7. A method according to claim 1, wherein the formation fluid information is acquired from formation fluid while downhole or at the surface.

8. A method according to claim 1, wherein the formation fluid information includes a temperature, the temperature being variable.

9. A method for estimating a formation fluid property comprising:
acquiring formation fluid information, the formation fluid information including pressure and volume;
extracting monotonic formation fluid information from the formation fluid information;
constructing an information set from the monotonic formation fluid information;
estimating a first partial derivative and a second partial derivative of the volume with respect to pressure from the information set;
estimating a first maxima from a volume acceleration sequence; and
estimating the formation fluid property at least in part by using the estimated first maxima.

10. A method according to claim 9, further comprising:
searching a set of local maxima points from the volume acceleration sequence before estimating the first maxima.

11. A method according to claim 9, further comprising:
storing a value of the estimated formation fluid property in a computer-readable medium.

12. A method according to claim 9, wherein the formation fluid property comprises a lower limit of the bubble point pressure.

13. A method according to claim 9, wherein the formation fluid property is a pressure, wherein the pressure is estimated using the information set at the pressure corresponding to the first maxima of the volume acceleration sequence.

14. A method according to claim 9, wherein the formation fluid information includes a temperature, the temperature being variable.

15. A method for estimating a formation fluid property comprising:
acquiring formation fluid information, the formation fluid information including pressure and volume;
extracting monotonic formation fluid information from the formation fluid information;
constructing an information set from the monotonic formation fluid information;
establishing a first linear regression model with the pressure, volume, temperature information set;
estimating a confidence interval using the first linear regression model;
determining a first pressure point beyond the confidence interval; and
estimating the fluid property at a second pressure point that is within the confidence interval.

16. A method according to claim 15, further comprising:
storing a value of the estimated formation fluid property in a computer-readable storage medium.

17. A method according to claim 15, wherein constructing information set establishing a first linear regression model estimating a confidence interval and determining a first pressure point are performed in an iterative manner.

18. A method according to claim 15, wherein the formation fluid property comprises an upper limit of the bubble point pressure.

19. A method according to claim 15, wherein the formation fluid information is acquired from a formation fluid while downhole.

20. A method according to claim 15, wherein the formation fluid information is acquired from a formation fluid sample at the surface.

* * * * *